United States Patent
Johnson et al.

(10) Patent No.: US 11,253,722 B2
(45) Date of Patent: *Feb. 22, 2022

(54) PHOTOBIOMODULATION THERAPY TO TREAT A DEGENERATIVE CONDITION OF THE RETINA AND/OR THE OPTIC NERVE

(71) Applicant: MULTI RADIANCE MEDICAL, Solon, OH (US)

(72) Inventors: Douglas Johnson, Brownstown, MI (US); Max Kanarsky, Solon, OH (US)

(73) Assignee: MULTI RADIANCE MEDICAL, Solon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/289,778

(22) PCT Filed: Oct. 30, 2019

(86) PCT No.: PCT/US2019/058754
§ 371 (c)(1),
(2) Date: Apr. 29, 2021

(87) PCT Pub. No.: WO2020/092495
PCT Pub. Date: May 7, 2020

(65) Prior Publication Data
US 2021/0308482 A1    Oct. 7, 2021

Related U.S. Application Data

(60) Provisional application No. 62/752,467, filed on Oct. 30, 2018.

(51) Int. Cl.
*A61N 5/06* (2006.01)
*A61N 5/067* (2006.01)

(52) U.S. Cl.
CPC ............ *A61N 5/0622* (2013.01); *A61N 5/067* (2021.08); *A61N 2005/0648* (2013.01);
(Continued)

(58) Field of Classification Search
CPC .......... A61N 5/0622; A61N 2005/0648; A61N 2005/0652; A61N 2005/0659;
(Continued)

(56) References Cited

U.S. PATENT DOCUMENTS 10,744,341 B2 *   8/2020   Johnson ............... A61F 9/0079
2003/0002297 A1   1/2003   Nemtsev
(Continued)

FOREIGN PATENT DOCUMENTS

DE    102013017586 A1    5/2015
EP         2008688 A1    12/2008
EP         3028742 A1    6/2016

OTHER PUBLICATIONS

EP Search Report dated Jul. 13, 2021 for Corresponding EP Application No. 18871936.3.
(Continued)

*Primary Examiner* — Jonathan T Kuo
(74) *Attorney, Agent, or Firm* — Tarolli, Sundheim, Covell & Tummino LLP

(57) ABSTRACT

Photobiomedulation therapy (PBMT) can be applied to the eye to treat optical neuritis, a sign of multiple sclerosis (MS). The light of PBMT can be directed into the eye, regardless of the position of the eye, by a device that includes an array of light delivery devices and a heat sink lens. The device can be placed proximal to the eye to direct the light into the eye. The light can have one or more wavelengths from 400-1100 nm and can be applied in at least one of a pulsed operating mode, a continuous operating mode, and a super-pulsed operating mode through the light source device to the skeletal muscle. The light signal is applied for a time sufficient to stimulate a phototherapeutic response in the retina and/or the optic nerve. PBMT applied in this manner provides a noninvasive, safe and effective treatment for optic neuritis.

18 Claims, 5 Drawing Sheets

(52) U.S. Cl.
CPC .............. *A61N 2005/0652* (2013.01); *A61N 2005/0659* (2013.01); *A61N 2005/0662* (2013.01)

(58) Field of Classification Search
CPC ...... A61N 2005/0662; A61N 2005/067; A61N 5/06–2005/073; A61F 9/008–2009/00897
See application file for complete search history.

(56) References Cited

U.S. PATENT DOCUMENTS

| | | |
|---|---|---|
| 2015/0057701 A1 | 2/2015 | Kelleher |
| 2015/0205146 A1 | 7/2015 | Legerton et al. |
| 2016/0067086 A1 | 3/2016 | Tedford et al. |
| 2016/0166849 A1 | 6/2016 | Dotson |
| 2017/0106201 A1 | 4/2017 | Schwarz |
| 2017/0128736 A1 | 5/2017 | Johnson |

OTHER PUBLICATIONS

Antonialli, F. C., et al. (2014). Phototherapy in skeletal muscle performance and recovery after exercise: effect of combination of super-pulsed laser and light-emitting diodes. Lasers in Medical Science, vol. 29 No.6, pp. 1967-1976 doi:10.1007/s10103-014-1611-7.
Grandinetti, V., et al. (2015). The thermal impact of phototherapy with concurrent super-pulsed lasers and red and infrared LEDs on human skin. Lasers in Medical Science, vol. 30 No. 5, pp. 1575-1581. doi:10.1007/s10103-015-1755-0.
International Search Report and Written Opinion dated Jan. 23, 2020 for Application No. PCT/US2019/58754.

* cited by examiner

PHOTOBIOMODULATION THERAPY TO TREAT A DEGENERATIVE CONDITION OF THE RETINA AND/OR THE OPTIC NERVE

CROSS-REFERENCE TO RELATED APPLICATIONS

This application is a national stage entry of PCT Appl. No. PCT/US19/058754, filed Oct. 30, 2019, entitled "PHOTOBIOMODULATION THERAPY TO TREAT A DEGENERATIVE CONDITION OF THE RETINA AND/OR THE OPTIC NERVE", which claims the benefit of U.S. Provisional Application No. 62/752,467, filed Oct. 30, 2018, entitled "PHOTOBIOMODULATION THERAPY TO TREAT A DEGENERATIVE CONDITION OF THE RETINA AND/OR THE OPTIC NERVE". This provisional application is hereby incorporated by reference in its entirety for all purposes.

TECHNICAL FIELD

The present disclosure relates generally to photobiomodulation therapy (PBMT) and, more specifically, to systems and methods that apply PBMT into the eye of a patient affected by a degenerative condition of the retina and/or the optic nerve to treat the degenerative condition of the retina and/or the optic nerve.

BACKGROUND

Multiple Sclerosis (MS) is a chronic, progressive disease of the central nervous system (CNS) that affects approximately 2.5 million people worldwide. MS often manifests itself through optic neuritis, an inflammatory demyelinating disease of the optic nerve. Although most commonly associated with MS, optic neuritis can occur in connection with other autoimmune disorders, viral infections, and drug toxicities. Major symptoms of optic neuritis may manifest in one or both eyes and include the sudden loss of vision, which may be partial or complete, sudden blurred or foggy vision, and/or pain associated with moving the affected eye.

Normally, patients with optic neuritis are treated with intravenous corticosteroids. However, it has been shown that corticosteroids have no benefit with regard to the return to normal visual function. In most patients with optic neuritis, visual function spontaneously improves over 2-3 months, but up to 60% of patients with optic neuritis who are treated with corticosteroids fail to return to normal visual function, with their vision remaining compromised. Accordingly, there is a need for a treatment modality that facilitates the return to normal visual function.

SUMMARY

The present disclosure relates generally to photobiomodulation therapy (PBMT) and, more specifically, to systems and methods that apply PBMT into the eye of a patient affected by a degenerative condition of the retina and/or the optic nerve to treat the degenerative condition of the retina and/or the optic nerve. PBMT provides a noninvasive, safe and effective therapy to harness the capacity of damaged cells in the retina and/or the optic nerve to self-repair helping the patient return to normal visual function. PBMT can be used alone or in combination with traditional therapies, like intravenous corticosteroids, to hasten the return to normal visual function.

In one aspect, the present disclosure can include a method for applying PBMT to treat a degenerative condition of the retina and/or the optic nerve. The method can include placing a light source device proximal to an eye of a patient affected by a degenerative condition of a retina and/or an optic nerve and applying a light signal in at least one of a pulsed operating mode, a continuous operating mode, and a super-pulsed operating mode through the light source device into the eye of the patient affected by the degenerative condition of the retina and/or the optic nerve. The light signal can be applied in at least one of a pulsed operating mode, a continuous operating mode, or a super-pulsed operating mode. The light signal can be applied for a time sufficient to stimulate a phototherapeutic response in the retina and/or the optic nerve of the patient affected by the degenerative condition of the retina or the optic nerve.

In another aspect, the present disclosure can include a system that can apply PBMT into the eye of a patient suffering from a degenerative condition of the retina and/or the optic nerve. The system can include a device configured for placement over at least a portion of a patient's eye socket to deliver light into the patient's eye to treat the degenerative condition of the retina and/or the optic nerve. The device can include a printed circuit board comprising an array of light delivery devices to provide the light; and a lens comprising a plurality of ridges that provide a heat sink for the light delivery devices. The system can also include a controller to power the printed circuit board and to provide a dosage of the light to treat the degenerative condition of the retina and/or the optic nerve.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
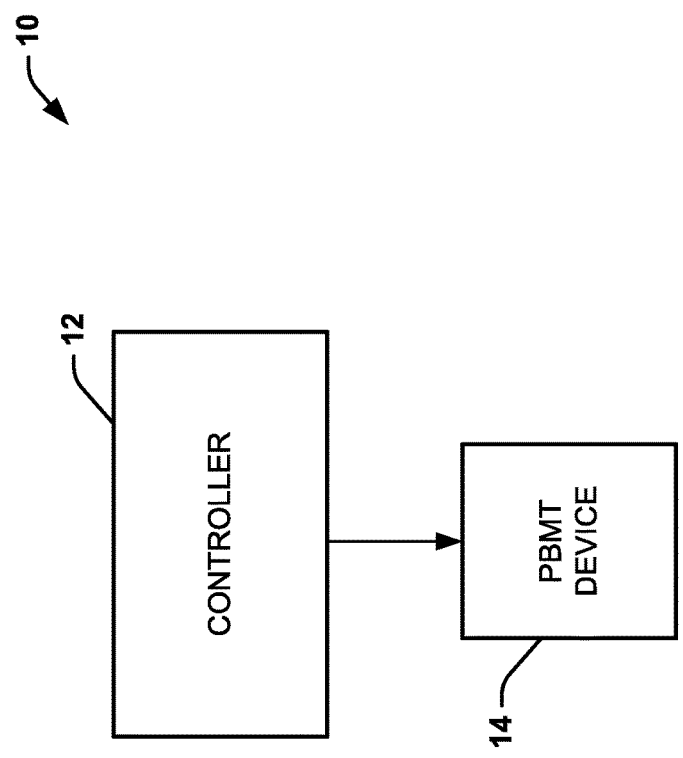
FIG. 1 is a block diagram illustration showing an example of a system that directs light into the eye of a patient affected by a degenerative condition of the retina and/or the optic nerve in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "multiple sclerosis (MS)" refers to an autoimmune disease in which the body's immune system attacks and destroys myelin in the central nervous system (CNS), leading to scarring and, eventually, deterioration or damage of the nerves themselves.

As used herein, the term "central nervous system (CNS)" refers to a division of the nervous system that integrates and coordinates the activities of the entire body. The CNS includes the brain, spinal cord, and optic nerves.

As used herein, the term "optic nerve" refers to a connection between one eye and the brain. Each optic nerve is part of the second pair of cranial nerves. The optic nerve transmits impulses to the brain that are formed by the retina to the visual cortex of the brain, which interprets the impulses as images.

As used herein, the term "eye" refers to an organ of sight. The eye has a number of components, including (but not limited to) the cornea, the iris, the pupil, the lens, the retina, the macula, the optic nerve, the choroid, and the vitreous.

As used herein, the term "retina" refers to a nerve layer that lines the back of the eye, including cells that are sensitive to light and that trigger nerve impulses that pass via the optic nerve to the brain, where a visual image is formed. In other words, the retina receives light and converts the light into a neural signal.

As used herein, the term "myelin" refers to the fatty substance that surrounds and insulates nerve fibers (also referred to as axons) to speed conduction in the nerve fibers. For example, the fibers of the optic nerve are myelinated.

As used herein, the term "photobiomodulation" refers to the application of a light signal to a portion of a subject's body to induce a phototherapeutic response in cells within the portion of the subject's body.

As used herein, the term "photobiomodulation therapy (PBMT)" refers to a drug-free, non-invasive treatment procedure, in which a light signal is applied to a certain region of a subject's body to treat a certain medical condition (e.g., pain, injury, disorder, disease, or the like) with a goal of ameliorating the certain medical condition via a phototherapeutic response. In some instances, PBMT can be used alone to induce a phototherapeutic response, but in other instances, PBMT can be used in combination with other therapies (e.g., a pharmaceutical therapy).

As used herein, the term "phototherapeutic response" refers to a biological reaction to application of PBMT to a portion of the patient's body.

As used herein, the term "light signal" refers to light having at least one wavelength. However, the light signal may include a combination of lights having wavelengths that create a synergistic effect when combined and improves the percentage of available light at greater tissue depths. In some instances, the wavelengths can be within a wavelength range of 400-1100 nm. For example, the wavelengths can include at least one wavelength corresponding to the visible range of the electromagnetic spectrum (e.g., red light) and at least one wavelength corresponding to the near-infrared or infrared range of the electromagnetic spectrum.

As used herein, the term "printed circuit board" refers to a mechanism to mechanically support and electrically connect electrical components (like light delivery devices) using conductive tracks, pads, and other features etched from one or more sheet layers of a conductive material (like copper) laminated onto and/or between sheet layers of a non-conductive substrate. The printed circuit board can be rigid and/or flexible.

As used herein, the term "light delivery device" also referred to as "light source", refers to an electrical component that can provide light at least one wavelength upon receiving an electrical signal. For example, the light source can be a low-level laser source (e.g., a laser light emitting diode (LED)) that generates coherent light). As another example, the light source can be an incoherent light source, such as a traditional LED.

As used herein, the term "light source device" refers to a mechanical implement that can deliver a light signal of PMBT to a portion of the subject's body. The light source device can include one or more light delivery devices.

As used herein, the term "light source" refers to a component of a light source device that delivers one or more lights of different wavelengths. For example, the light source can be a low-level laser source (e.g., a laser light emitting diode (LED)) that generates coherent light. The low-level laser source can operate in a super pulsed mode that generates ultrashort pulses with a high peak power and minimal heat. As another example, the light source can be an incoherent light source, such as a traditional LED or light bulb. The incoherent light source can operate in a pulsed mode and/or a continuous mode.

As used herein, the term "proximal" refers to a location that is near a target (e.g., the eye). For example, a device that is located proximal at least a portion of the eye can be located over the at least the portion of the eye, but need not be directly over the center of the area in the at least the portion of the eye.

As used herein, the term "sufficient" refers to an amount adequate enough to satisfy a condition. For example, "a time sufficient to stimulate a phototherapeutic response in a retina and/or an optic nerve" can refer to a light signal being applied into an eye for a time adequate enough to stimulate the phototherapeutic response in the retina and/or the optic nerve.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to photobiomodulation therapy (PBMT) and, more specifically, to systems and methods that apply PBMT into the eye of a patient affected by a degenerative condition of the retina and/or the optic nerve to treat the degenerative condition of the retina and/or the optic nerve. One such degenerative condition is optic neuritis, a primary inflammation of the optic nerve occurring in autoimmune diseases, viral infections, and drug toxicities. Optic neuritis may lead to cell death in the retinal and optic nerve, eventually causing blindness. Application of PBMT, according to certain therapy parameters, through the eye, can stimulate a phototherapeutic response that can counteract this cell death and eventual blindness. PBMT can be used as an independent therapy strategy. However, in some instances, a greater benefit may be seen if the PBMT is performed as an adjunct to existing therapeutic agents, including intravenous corticosteroids.

III. Photobiomodulation Therapy (PBMT)

Mitochondrial dysfunction and oxidative stress play a key role in the pathogenesis of optic neuritis and other degenerative conditions of the retina and optic nerve. Such neurodegeneration can be due to a decreased mitochondrial oxidative capacity and a decrease in mitochondrial function. The decreased mitochondrial oxidative capacity can improve due to modulation of mitochondrial cytochrome c-oxidase (CCO) (a photoacceptor), the phototherapeutic response triggered by the PBMT. Modulating CCO can lead to stopping or slowing the neurodegeneration characteristic of optic neuritis and other degenerative conditions of the retina and optic nerve.

While not wishing to be bound by theory, there is strong evidence to suggest that one of the basic mechanisms of PBMT is the acceleration of electron transfer by electromagnetic radiation in the visible and near infrared region of the spectrum, via the modulation of CCO activity. Accordingly, PBMT acts on mitochondria-mediated signaling pathways to preserve mitochondrial function, attenuate oxidative stress, stimulate the production of cytoprotective factors, and prevent neuronal death. Traditionally, PBMT has attempted to modulate CCO activity using a single wavelength in the visible or near infrared region of the spectrum. However, the use of such single wavelengths cannot effectively modulate CCO activity since the single wavelength is limited by its specific absorption spectrum. The light signal used herein has a combination of wavelengths, which are used concurrently, providing an overlapping effect of peak activation, which accelerates CCO activity. Additionally, the time of CCO activation is prolonged across the entire therapeutic window by delivering much smaller doses across many wavelengths, rather than a single wavelength of a greater power. The multiple wavelengths enhance adenosine triphosphate (ATP) production, requiring less energy, and provides continual photodissociation of nitric oxide (NO), not only from CCO, but also from intracellular stores like nitrosylated forms of hemoglobin. NO is a potent vasodilator and PBMT can increase the vasodilation due to NO and increases the availability of oxygen to treated cells, and allows for greater traffic of immune cells into tissue.

IV. Systems

One aspect of the present disclosure can include a system 10 (FIG. 1) that directs light into a patient's eye to treat a degenerative condition of the retina and/or the optic nerve. The PBMT can cause a phototherapeutic response in the retina and/or the optic nerve, reducing neurodegeneration characteristic of MS. The phototherapeutic response can decrease neurodegeneration by improving mitochondrial oxidative capacity due to modulation of mitochondrial cytochrome c-oxidase (CCO). Accordingly, the PBMT provides a noninvasive, safe and effective therapy to treat degenerative optical conditions. PBMT can be used as an independent therapy strategy for patients with a degenerative optical condition. However, in some instances, a greater benefit may be seen if the PBMT is performed as an adjunct to existing therapeutic agents, such as intravenous corticosteroids.

The system 10 includes a controller 12 and a PBMT device 14. The controller 12 can provide power to the PBMT device 14, which can generate the light and can be configured to direct the light into the patient's eye. At least a portion of the PBMT device 14 can be configured for placement over and/or proximal to the patient's eye. The PBMT device 14 can be in the form of a patch, a light bridge, glasses, or the like. Additionally, the PBMT device may be coupled to an anchor, like a strap, to hold the PBMT device in place proximal to the patient's eye.

The controller 12 can control parameters of the PBMT device 14. When used on the eye, the light used for PBMT can have one or more wavelengths between 400 nm and 1100 nm and an energy density of 20 mW/cm2 to 75 mW/cm$^2$ applied for a time (e.g., between 30 seconds and 5 minutes). In some instances, two or more wavelengths can be combined for a single PBMT treatment. In other instances, three or more wavelengths can be combined for a single PBMT treatment. For example, one or more wavelengths between 600 nm-700 nm and one or more wavelengths between 800-950 nm. As another example, one or more wavelengths between 630 nm-650 nm and one or more wavelengths between 840 nm-880 nm.

The PBMT device 14 can be configured to cover at least a portion of a patient's eye socket and direct the light through the pupil and into the eye. The PBMT device 14 includes a printed circuit board with an array of light delivery devices arranged to direct the light through the pupil. The PBMT device 14 also includes a lens that includes a plurality of ridges that provide a heat sink for the array of light delivery devices.

The controller 12 can provide power to at least a portion of the PBMT device 14, which can generate light when powered. The PBMT device can be shaped to direct the light into (or through) the patient's eye. An advantage of the system 10 compared to conventional light delivery solutions is that the PBMT device 14 is configured to direct the light into the patient's eye regardless of the orientation of the patient's eye. This allows the patient's eye to receive the benefits of PBMT described above. The system 10 is designed so the patient can receive the PBMT either in the clinic or at home. To this end, the PBMT device 14 can be can be dust tight and waterproof (e.g., at least IP 65).

Figure 2:
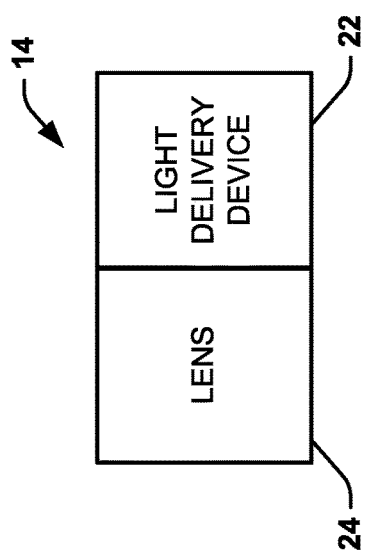
FIG. 2 is a block diagram illustration showing an example of the PBMT device of FIG. 1.

The PBMT device 14 can include at least a light delivery device 22 that generates the light and a lens 24 that facilitates delivery of the light, as shown in FIG. 2. Note that the PBMT device 14 can include additional components to facilitate the delivery of the light through the patient's eye. The PBMT device 14 can be shaped further ensure delivery of the light through the patient's eye. At least a portion of the lens 24 and/or the light delivery device 22 can be flexible. However, in some instances, at least a portion of the lens 24 and/or the light delivery device 22 can be rigid.

Figure 3:
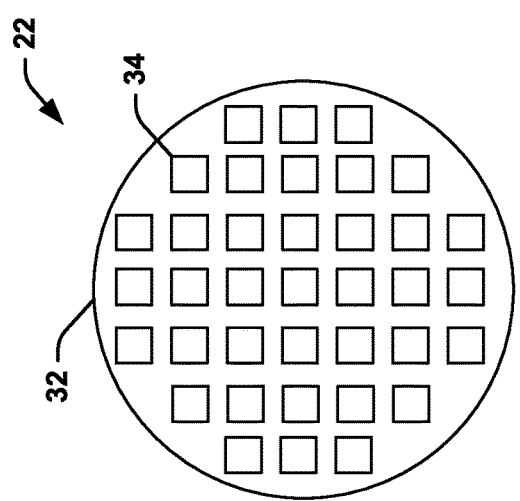
FIG. 3 is a block diagram illustration showing an example light delivery device of FIG. 2.

An example of the light delivery device 22 is shown in FIG. 3. The light delivery device 22 can include an array of light delivery devices 34 (e.g., one or more) arranged regularly on a printed circuit board 32. The light delivery devices 34 can be light emitting diodes, laser diodes, or the like. In some instances, the light delivery devices 34 can each (individually) generate light with a wavelength from 400 nm to 1100 nm. In other instances, the light delivery devices 34 can each (individually) generate light with a wavelength from 630 nm to 670 nm and/or from 800 nm to 950 nm. The regular arrangement of the light delivery devices 34 with uniform spacing can contribute to the uniform delivery of light (in other words, the light is delivered at a uniform density). Each of the light delivery devices 34 can deliver a unique light signal from a unique position. The printed circuit board 32 can be flexible and/or rigid.

Figure 4:
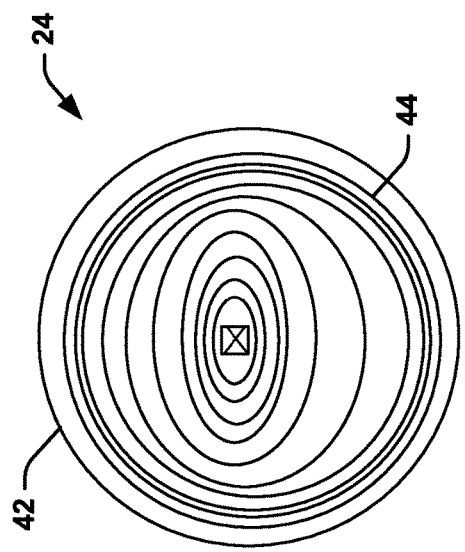
FIG. 4 is a diagram illustration showing an example lens of FIG. 2.

An example of the lens 24 is shown in FIG. 4. The lens 24 can be flexible and can overlay the light delivery device 22 to facilitate delivery of the light through the eye. The lens 24 can include a base 42 and a plurality of ridges 44 that provide a heat sink for the light delivery devices 34. The heat sink absorbs heat from the light delivery devices 34 so that the heat is not transmitted to the eye. At least a portion of the lens 24 can be injected with an antimicrobial or antibacterial element or compound (such as one containing silver). The lens 24 can be constructed of any material that facilitates delivery of light (e.g., silicon, silicone, etc.).

The controller 12 of system 10 can deliver power according to a wired connection and/or a wireless connection. The controller 12 can include an internal battery and/or external power receiver/storage to provide power to at least a portion of the electronics of the PBMT device 14 required for operation of the system 10. In some instances, the controller 12 can be a unit external to the PBMT device 14 (e.g., similar to a TENS device). In other instances, the controller 12 can be included with the PBMT device 14 (e.g., in the periphery of the PBMT device 14). In still other instances, the controller 12 can be located on or within a device proximal to the PBMT device (e.g., a strap device).

The controller 12 can receive and/or provide AC and/or DC current. Notably, the controller can include a log generator that is only accessible to previously approved users (e.g., a doctor or hospital). The previously approved users can be associated with user names associated with permissions that allow access to the logs. However, the logs can be transmitted to computers associated with the permitted users. The logs can include data related to user of the PBMT—such as when, where, how often, and the like.

Figure 5:
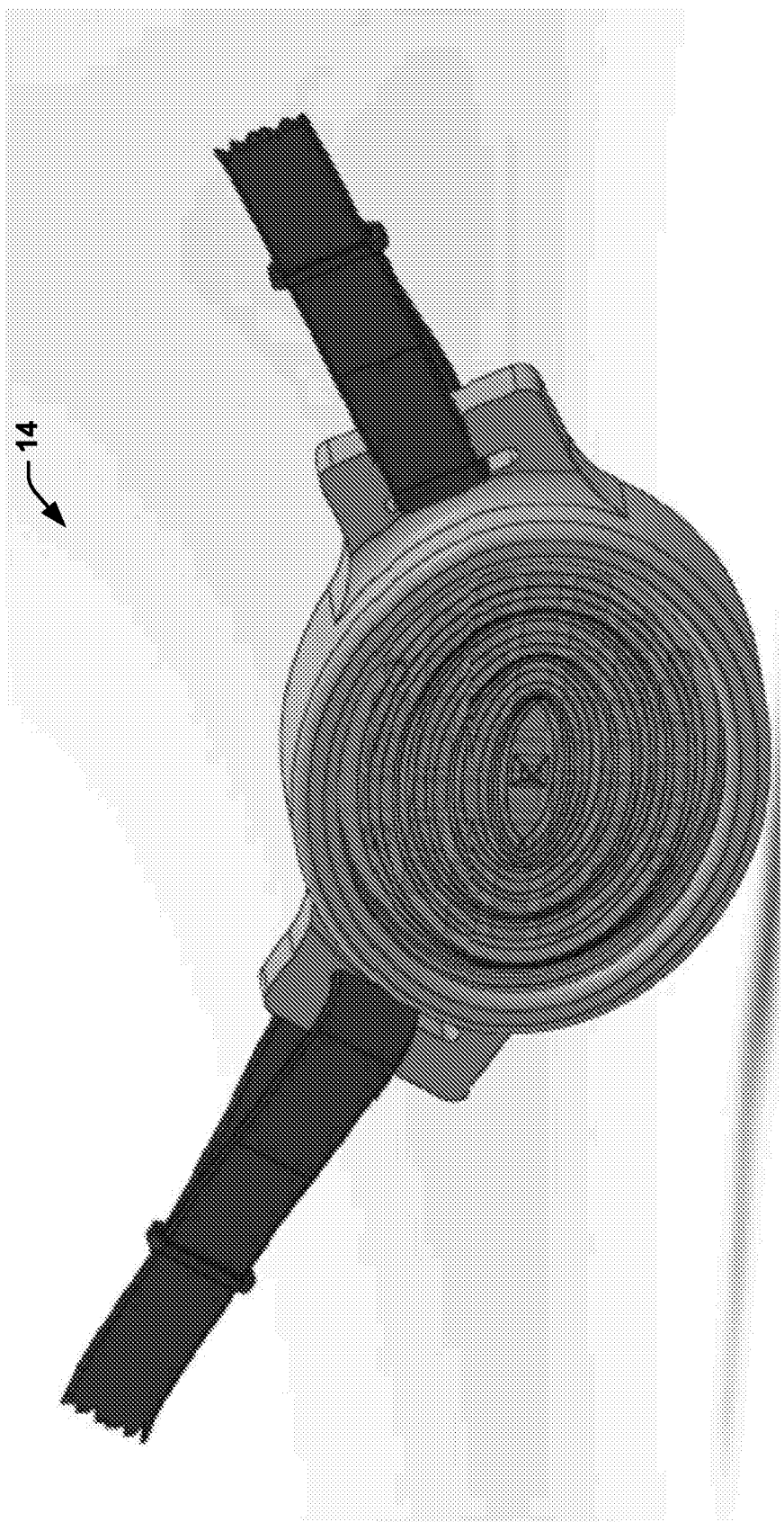
FIG. 5-6 illustrate an example device that can be used to implement the system of FIG. 1.
Figure 6:
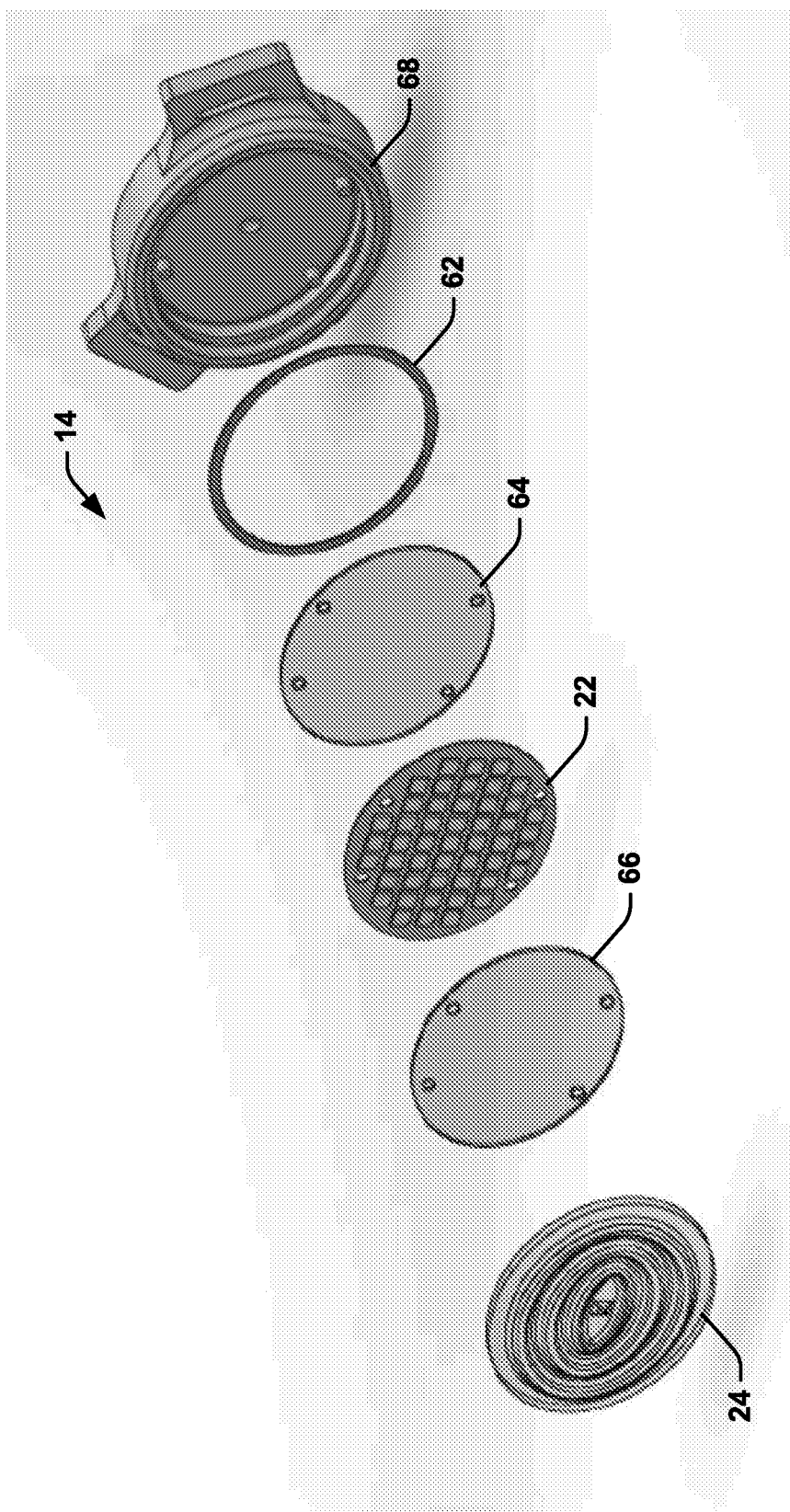
Figure 7:
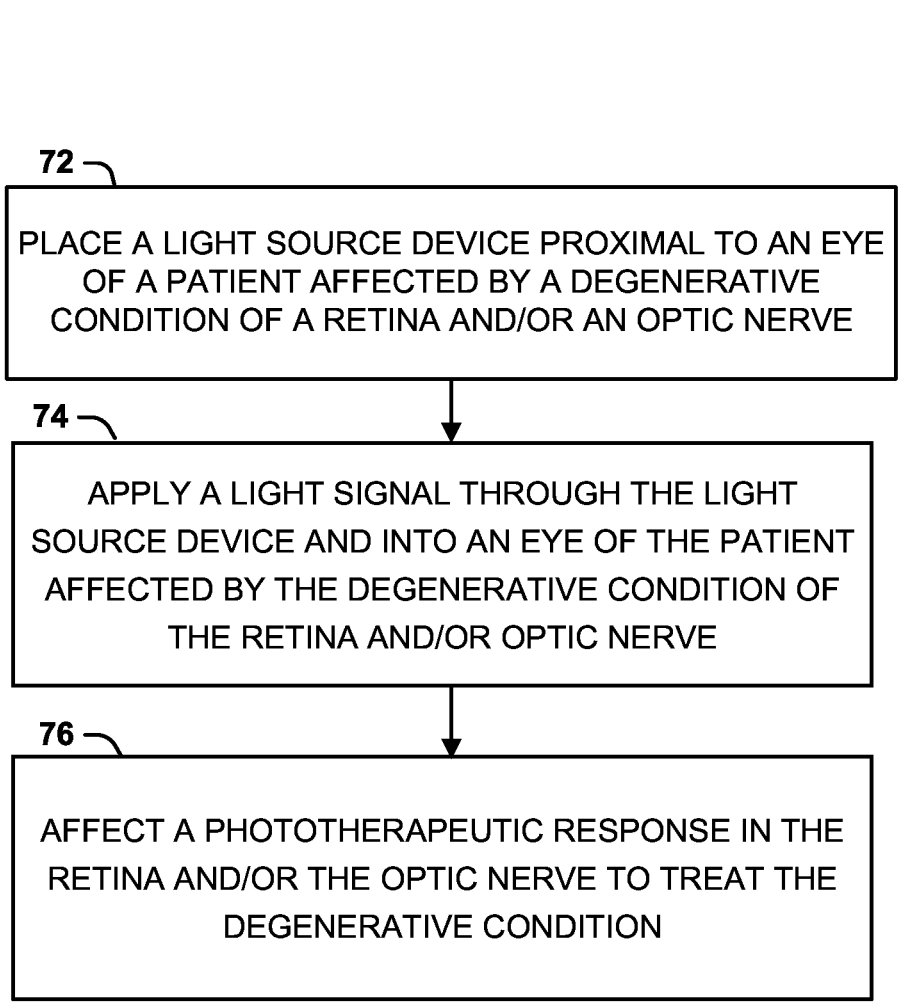
FIG. 7 is a process flow diagram of an example method for treating a degenerative condition of the retina and/or the optic nerve in accordance with another aspect of the present disclosure.

FIGS. 5 and 6 provide an illustration of an example PBMT device 14 that can be used in the system 10. FIG. 5 provides a view from an eye looking through the lens to receive the PBMT. This PBMT device 14 can include a strap to anchor the device in position over the eye. FIG. 6 shows the components of the device shown in FIG. 5. The lens 24 (shaped to the eye, made of silicon with concentric rings) and the light delivery device 22 (flexible design) are separated by a Mylar layer 66 made of a Mylar sheet to further facilitate the homogeneous, uniform density of light (to facilitate diffusion of the light). Another Mylar layer 64 is located behind the light delivery device 22. The device also includes a flexible metallic ring 62 to conform the lens 24 and the light delivery device 22 to a shape of the patient's eye to direct the light through the patient's eye and into the patient's pupil. The device also includes a component 68 to anchor the layers therewithin. As shown in FIGS. 5 and 6, the component 68 can mate with the anchor (in this case the strap). Moreover, the component 68 can be opaque to better focus the light into the patient's eye. Each of the layers 24, 66, 22, and 64 can include holes to attach to pegs within the component 68.

V. Methods

Another aspect of the present disclosure can include a method 70 for treating a degenerative condition of the retina and/or the optic nerve. The method 70 can be executed by hardware—for example, at least a portion of the system 10 shown in FIG. 1 and described above. Additionally, PBMT can be used alone or in combination with a traditional pharmaceutical therapy to treat a degenerative condition of the retina and/or the optic nerve.

The method 70 is illustrated as process flow diagrams with flowchart illustrations. For purposes of simplicity, the method 70 shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 70. Additionally, one or more elements that implement the method 70, such as PBMT device 14 and/or controller 12 of FIG. 1, may include a non-transitory memory and one or more processors that can facilitate the configuration and generation of the light signal.

At step 72, a light source device can be placed proximal to an eye of a patient affected by a degenerative condition of a retina or an optic nerve. The light source (e.g., the PBMT device 14) can be designed to direct light uniformly into the patient's eye, regardless of orientation of the patient's eye. At step 74, a light signal can be applied through the light source device (e.g. PBMT device 14) and into the eye of the patient affected by the degenerative condition of the retina or optic nerve. The light signal can be generated in at least one of a pulsed operating mode, a continuous operating mode, and a super-pulsed operating mode. The light signal can include one wave of a single wavelength. However, alternatively, the light signal can include a plurality of individual waves with multiple wavelengths. The combination of the plurality of individual waves can work constructively to create a synergistic effect, enhancing each individual wavelength's ability to penetrate the skin, allowing for a greater portion of the available light energy to reach biological targets in the retina and/or the optic nerve. The light signal is applied for a time sufficient to stimulate a phototherapeutic response the retina and/or the optic nerve.

At step 76, a phototherapeutic response can be affected in the retina and/or the optic nerve to treat the degenerative condition. The phototherapeutic response can include improving mitochondrial oxidative capacity due to modulation of mitochondrial cytochrome c-oxidase (CCO). As a result, the patient will be able to return to normal visual function.

VI. Experimental

The following example is shown for the purpose of illustration only and is not intended to limit the scope of the appended claims. This experiment demonstrates the therapeutic potential and mechanism of action of photobiomodulation therapy (PBMT)—using near infrared light—on the eye to treat optic neuritis. The PBMT can be delivered as a single wavelength (e.g., 670 nm) and/or a triple wavelength (660, 830, 905 nm).

Experimental Autoimmune Encephalomyelitis (EAE) induced with myelin oliogendrocyte glycoprotein in C57BL/6 mice is the primary animal model of experimental optic neuritis. Mitochondrial dysfunction and oxidative stress play a key role in the pathogenesis optic neuritis and other acute toxicities and degenerative conditions of the retina and optic nerve. Importantly, recent studies have shown that retinal and optic nerve mitochondrial proteins including components of the mitochondrial electron transport chain are early targets in the pathogenesis of experimental optic neuritis. PBMT has been shown to augment mitochondrial function, stimulate protective pathways, and promote neuronal survival in a murine model of autoimmune optic neuritis.

Methods:

The proposed experiments are designed to investigate the efficacy and potential therapeutic mechanism(s) of photobiomodulation for the treatment of autoimmune optic neuritis using the EAE model. C57BL/6 (B6) mice will be humanely cared for in an AAALAC-accredited veterinarian supervised animal care facility on the UWM campus. Mice will be group housed in micro-isolation cages. All animals will be supplied food and water ad libitum and maintained on a 12 hr light/dark schedule in a temperature- and humidity-controlled environment. Animals will be handled in accordance with the Guide for the Care and Use of Laboratory Animals as adopted and promulgated by the National Institutes of Health.

EAE Model: EAE was induced in B6 mice by immunization with MOG according to our standard laboratory protocol. Clinical symptoms will be graded on a scale of 0-5 with increasing severity.

PBM Treatment Protocol: The majority of the experiments utilized 670 nm LED arrays to deliver a dose of 4.5 J/cm$^2$ (0.025 W/cm$^2$ for 180 seconds=4.5 J/cm$^2$. It is with this dose that preservation of optic nerve structure was noted. However, there is general agreement in the field that longer wavelengths of light (i.e., 810 nm or higher) will be necessary to obtain a clinical effect in human neurodegenerative diseases.

For this study, two treatment devices at 3 doses of light (1, 3 and 10 J/cm$^2$)-670 nm LED Array—Continuous wave emission, Diode Laser Array (660, 830 and 905 nm)—superpulsed emission were compared General Treatment Protocol: Treatment commenced on the day of clinical onset and will continue once daily for 7 days. Beginning on the third day of treatment, the structure & function of the optic nerve in each mouse were assessed by Optical Coherence Tomography (OCT). Animals were humanely euthanized at peak disease (16-20 dpi) and the eyes and optic nerves harvested.

670 nm LED Array Treatment Protocol: Mice were placed in a plexiglass restraint device and treated with 670 nm LED arrays [GaAlAs LED arrays, 670±20 nm at 50% power; Quantum Devices, Inc., Barneveld, Wis.], engineered to eliminate heat. The LED array ositioned directly over the animals at a distance of 2 cm. The entire mouse will be irradiated for 40, 120 and 400 s respectively at a fixed power density of 0.025 W/cm$^2$ (at the dorsal surface of the mouse) administered at 24 hour intervals. The total delivered energy for irradiated groups will be 1, 3, and 10 J, respectively. Sham-treated animals will be handled in the same way, except that they will not be exposed to the LED array.

Superpulsed Diode Array Treatment Protocol: Diode lasers with mean output power of 50 mW; spot size of 0.028 cm$^2$; continuous mode; and wavelengths of 660 nm (red), 830 nm (infrared), or 905 nm (infrared) will be used. The optical power will be calibrated using a Newport multifunction optical meter model 1835C. The entire mouse will be exposed to irradiation for 20, 60, and 200 s, respectively, with a fixed power density of 1.78 W/cm$^2$. The total delivered energy for irradiated groups will be 1, 3, and 10 J, respectively. Sham-treated animals will be handled in the same way, except that they will not be exposed to the diode array.

Results:

PBMT is effective in preventing the functional structural and immunohistopathological alterations associated with experimental autoimmune optic neuritis.—preventing retinal dysfunction, retinal ganglion cell death, optic nerve demyelenation degeneration in a murine model of MS.

Optokinetic Responses: Visual function was assessed by the optokinetic tracking response (OKR) using OptoMotry software and apparatus (Cerebral Mechanics). Briefly, mice were placed on a platform in a closed chamber and a virtual cylinder of a 100% contrast grating is projected at varying spatial frequencies. Mice were observed through a camera, and the investigator assessed whether the mice track the rotating cylinder. Visual function is reflected by the highest spatial frequency at which mice track and is recorded as cycles/degree. Mice only track in one direction with each eye, therefore separate vision measures were recorded for each eye by alternating the direction of rotation of the cylinder.

Spectral-Domain Optical Coherence Tomography (SD-OCT): Imaging in Live Mice In vivo high-resolution three-dimensional (3D) imaging of the live mouse retina was performed using SD-OCT (Bioptigen, Inc., Durham, N.C.). Briefly, the mice were anesthetized with an intraperitoneal injection of ketamine (80 mg/kg) and xylazine (5 mg/kg). Pupils were dilated with a drop of 1% tropicamide and lubricating eye drops (Systane Ultra; Alcon Laboratories, Inc., Fort Worth, Tex.) were applied to preserve the corneal hydration and to increase the clarity. The mice were restrained on a custom stage that was fixed on a six-axis platform, which allowed free rotation, to align the eye for imaging of the optic nerve head (ONH). Raster scans were performed for each eye.

Optic Nerve Histopathology: Histopathologic analysis of glutaraldehyde-fixed retina and optic nerve isolated at the peak disease was used to assess the neuroprotective potential of PBM as evidenced by decreased immune cell infiltration, decreased demyelination and decreased axonal loss. Briefly, mice will be anesthetized with ketamine/xylazine cocktail and perfused via cardiac puncture with 60 ml sterile saline. Eyes and attached optic nerves were dissected out and post-fixed in glutaraldehyde, embedded in EPON and sectioned at 6 μm. Sections were stained with toluidine blue for determination of demyelination and axonal loss, and graded on a scale of 0-5. Adjacent sections were stained with hematoxylin and eosin for determination of immune cell infiltration and graded on a scale of 0-5.

Characterization the effect of wavelength & dose on optic neuritis in the B6/MOG35-55 EAE mode: With 670 nm LED arrays at a set dose of 4 J/cm$^2$, preservation of optic nerve structure was noted. The effect of 660 nm light and 875 nm light delivered using an MR4 ACTIV (or similar unit) on optic neuritis at doses of 0.4 J/cm$^2$, 4 J/cm$^2$, and 40 J/cm$^2$ showed improvement compared to sham treated animals.

In an effort to elucidate the mechanisms of PBM induced neuroprotection, retinal and optic nerve CcO expression and mitochondrial bioenergetics coupled with pro-inflammatory and anti-inflammatory cytokines and established indices of oxidative and nitroxidative stress were evaluated.

Immunohistochemistry and TUNEL: Eyes and optic nerves for immunohistochemical evaluation were immersion-fixed in 4% paraformaldehyde, cryoprotected, embedded in Tissue-Tek OCT and cryosectioned at 14 μm. Antibodies against the following proteins were used: acrolein, a marker of lipid peroxidation; nitrotyrosine, a marker of nitroxidative stress; cytochrome oxidase IV subunit I (CO), a marker of mitochondrial oxidative function and manganese superoxide dismutase (MnSOD/SOD2), a critical antioxidant enzyme. After processing of sections, levels of fluorescent intensity will be assessed using confocal microscopy and optical densitometry (Image J). To assess the number of dying RGCs, sections were labeled with the TUNEL technique.

Characterization of the cytokine response: Retinae and optic nerves were dissected. Total RNA was prepared, followed by reverse transcription for analysis of cytokine expression by Taqman® real-time PCR expression assays. Retinal and optic nerve tissue were analyzed for the expression of the pro-inflammatory cytokines IFNγ and TNFα, and the anti-inflammatory cytokine IL-10.

Statistics: Statistical analyses will be performed by ANOVA for comparison of RGC numbers in control eyes versus EAE eyes with and without ON, and ANOVA of repeated measures for OKR responses. To compare RGC numbers in EAE eyes with control eyes, group means were compared by Student's t-tests. Statistics were performed using GraphPad Prism 5.0 (GraphPad Software, San Diego, Calif., USA).

Correlation of function data and histological preservation of the optic nerve in PBM-treated mice. Mice (N=20) were immunized with MOG35-55 for the induction of EAE according to standard lab protocol. Beginning on the day of onset, mice were randomly assigned into treatment groups. One group (N=10) received PBMT with the optimal wavelength & dose as determined above; the other group (N=10) received sham treatment. Beginning with the second day of treatment, OCT and ERG were performed, as above. Two mice were euthanized on day 2 of treatment from PBM treated & sham treated groups, following OCT/ERG, and perfused with 60 ml ice cold saline. The CNS (brain & spinal cord) were removed and post-fixed in 4% neutral buffered paraformaldehyde and stored at 4° C. for subsequent processing. Tissue were similarly removed from 3 mice in each group on the first day that OCT/ERG reveal clinical improvement in the PBM-treated group; at the peak of clinical EAE; and 7 days after the cessation of treatment. Tissue was embedded in EPON and subsequently sectioned (5 um) and stained with toluidine blue and hematoxylin/eosin (H&E) for histologic examination for demyelination and inflammation, respectfully.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A method comprising:
    placing a light source device proximal to an eye of a patient affected by a degenerative condition of a retina and/or an optic nerve;
    positioning the light source device over the eye of the patient affected by the degenerative condition of the retina to focus the light signal into the patient's eye; and
    applying a light signal in at least one of a pulsed operating mode, a continuous operating mode, and a super-pulsed operating mode through the light source device into the eye of the patient affected by the degenerative condition of the retina and/or the optic nerve, wherein the light signal is applied for a time sufficient to stimulate a phototherapeutic response in the retina and/or the optic nerve of the patient affected by the degenerative condition of the retina or the optic nerve,
    wherein the light source device comprises:
        a printed circuit board comprising an array of light delivery devices; and
        a flexible silicone lens comprising a plurality of ridges that provide a heat sink for the light delivery devices.

2. The method of claim 1, wherein the degenerative condition of the retina and/or the optic nerve is autoimmune optic neuritis.

3. The method of claim 1, wherein the phototherapeutic response prevents demyelination, maintains intact structure of myelin, or decreases inflammation of the optic nerve.

4. The method of claim 1, wherein the light source device is an eye patch, goggles, or glasses.

5. The method of claim 1, wherein the light source device is configured to direct the light signal through the patient's eye regardless of a position of the patient's eye.

6. The method of claim 1, wherein the light source device comprises an array of light delivery devices.

7. The method of claim 6, wherein the array of light delivery devices provide light with at least one wavelength from 400 nm to 1100 nm.

8. The method of claim 7, wherein the array of light delivery devices comprises light delivery devices each configured to operate in the pulsed operating mode, the continuous operating mode, or the super-pulsed operating mode.

9. A system comprising:
    a device configured for placement over at least a portion of a patient's eye socket to deliver light into the patient's eye to treat a degenerative condition of a retina and/or an optic nerve, comprising:
        a printed circuit board comprising an array of light delivery devices to provide the light; and
        a lens comprising a plurality of ridges that provide a heat sink for the light delivery devices; and
    a controller to power the printed circuit board and to provide a dosage of the light to treat the degenerative condition of the retina and/or the optic nerve.

10. The system of claim 9, wherein the array of light delivery devices comprises at least three light sources each configured to apply a portion of the light signal comprising a different wavelength within a wavelength range of 400-1100 nm.

11. The system of claim 10, wherein each of the at least three light sources operates in at least one of a pulsed operating mode, a continuous operating mode, or a super-pulsed operating mode.

12. The system of claim 10, wherein each of the at least three light sources is a light emitting diode or a laser diode.

13. The system of claim 9, wherein the device is an eye patch, goggles, or glasses with at least a portion configured to cover at least a portion of the patient's eye.

14. The system of claim 9, wherein the device comprises a flexible mechanism to focus the light into the patient's eye.

15. The system of claim 9, wherein the device comprises a mechanism to removeably secure to the patient's head.

16. The system of claim 9, wherein the device further comprises at least one MYLAR® (polyethylene terephthalate (PET) film) sheet to facilitate a homogeneous uniform density of the light.

17. The system of claim 16, wherein the device is configured to focus light to facilitate absorption by the patient's retina.

18. The system of claim 9, wherein the dosage is at least 0.4 J/cm$^2$.

* * * * *